United States Patent [19]
Forte

[11] Patent Number: 5,092,899
[45] Date of Patent: Mar. 3, 1992

[54] PROSTHESIS WITH FLEXIBLE INTRAMEDULLARY STEM

[76] Inventor: Mark Forte, 11 Oak La., Pine Brook, N.J. 07058

[21] Appl. No.: 434,514

[22] Filed: Nov. 14, 1989

Related U.S. Application Data

[63] Continuation of Ser. No. 171,373, Mar. 21, 1988, abandoned, which is a continuation-in-part of Ser. No. 849,172, Apr. 7, 1986, abandoned.

[51] Int. Cl.⁵ ............................................. A61F 2/32
[52] U.S. Cl. ......................................... 623/23; 623/18
[58] Field of Search ..................... 623/16, 18, 19, 20, 623/22, 23

[56] References Cited

U.S. PATENT DOCUMENTS

| | | | |
|---|---|---|---|
| 2,066,962 | 1/1937 | Cross | 273/80 B |
| 4,287,617 | 9/1981 | Tarnier | 623/23 |
| 4,520,511 | 6/1985 | Gianezio et al. | 623/23 |
| 4,570,271 | 2/1986 | Sump | 623/18 |
| 4,599,085 | 7/1986 | Riess et al. | 623/18 |
| 4,636,219 | 1/1987 | Pratt et al. | 623/22 |

FOREIGN PATENT DOCUMENTS

| | | | |
|---|---|---|---|
| 2933237 | 3/1981 | Fed. Rep. of Germany | 623/18 |
| 2933271 | 3/1981 | Fed. Rep. of Germany | 623/18 |

Primary Examiner—David J. Isabella
Attorney, Agent, or Firm—Klauber & Jackson

[57] ABSTRACT

An implant for a hip or other joint is provided. Briefly stated, an intramedullary stem is provided having flexibility which is comparable to that of the surrounding bone. A bore is disposed in the stem portion with the stem wall thickness uniform or varying from the proximal end to the distal end, depending upon the amount of flexibility desired. This flexibility therefore distributes the loading forces from the joint more uniformly over the supporting cortical bone with the result that bone degeneration from stress shielding is minimized or eliminated.

9 Claims, 6 Drawing Sheets

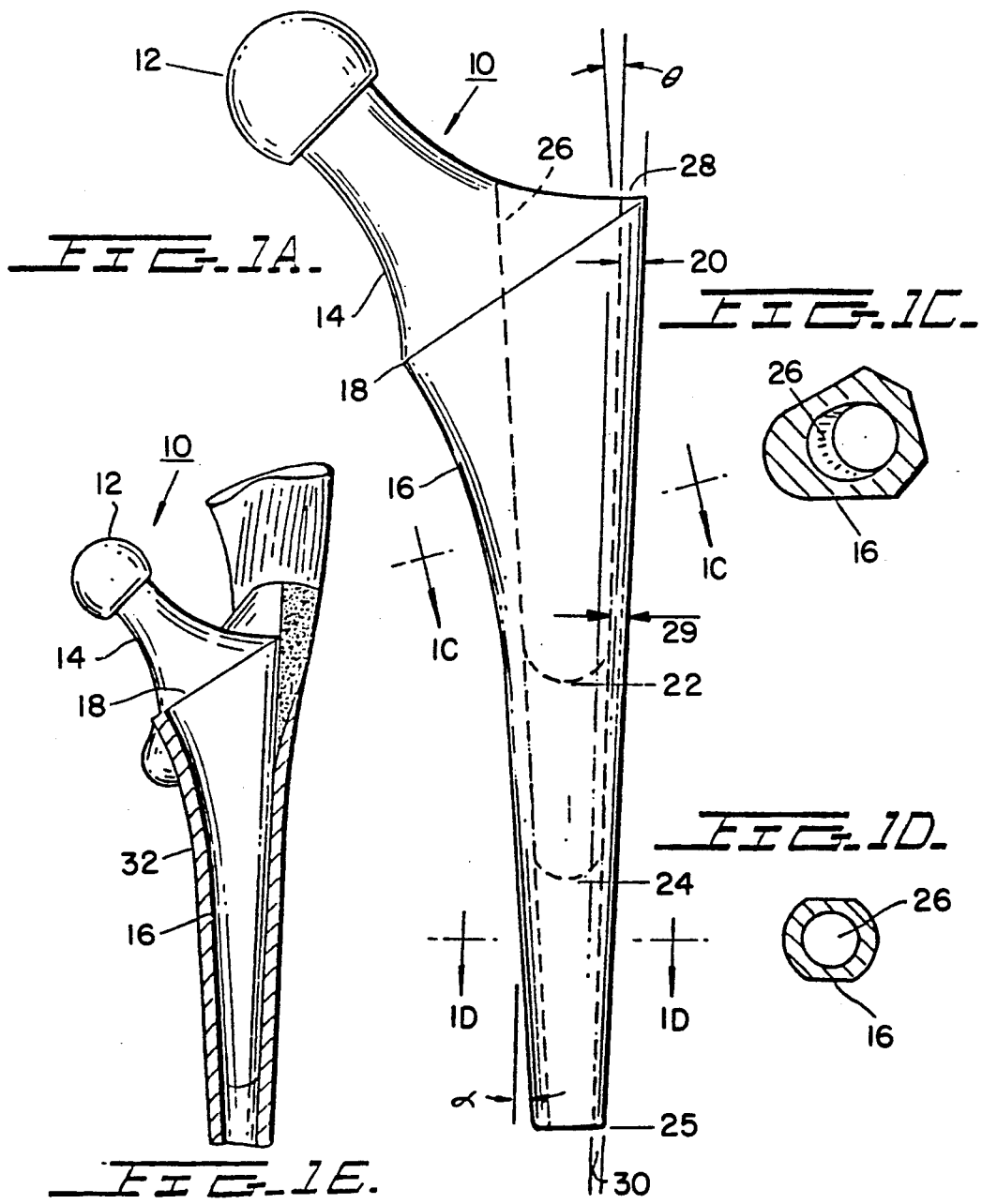

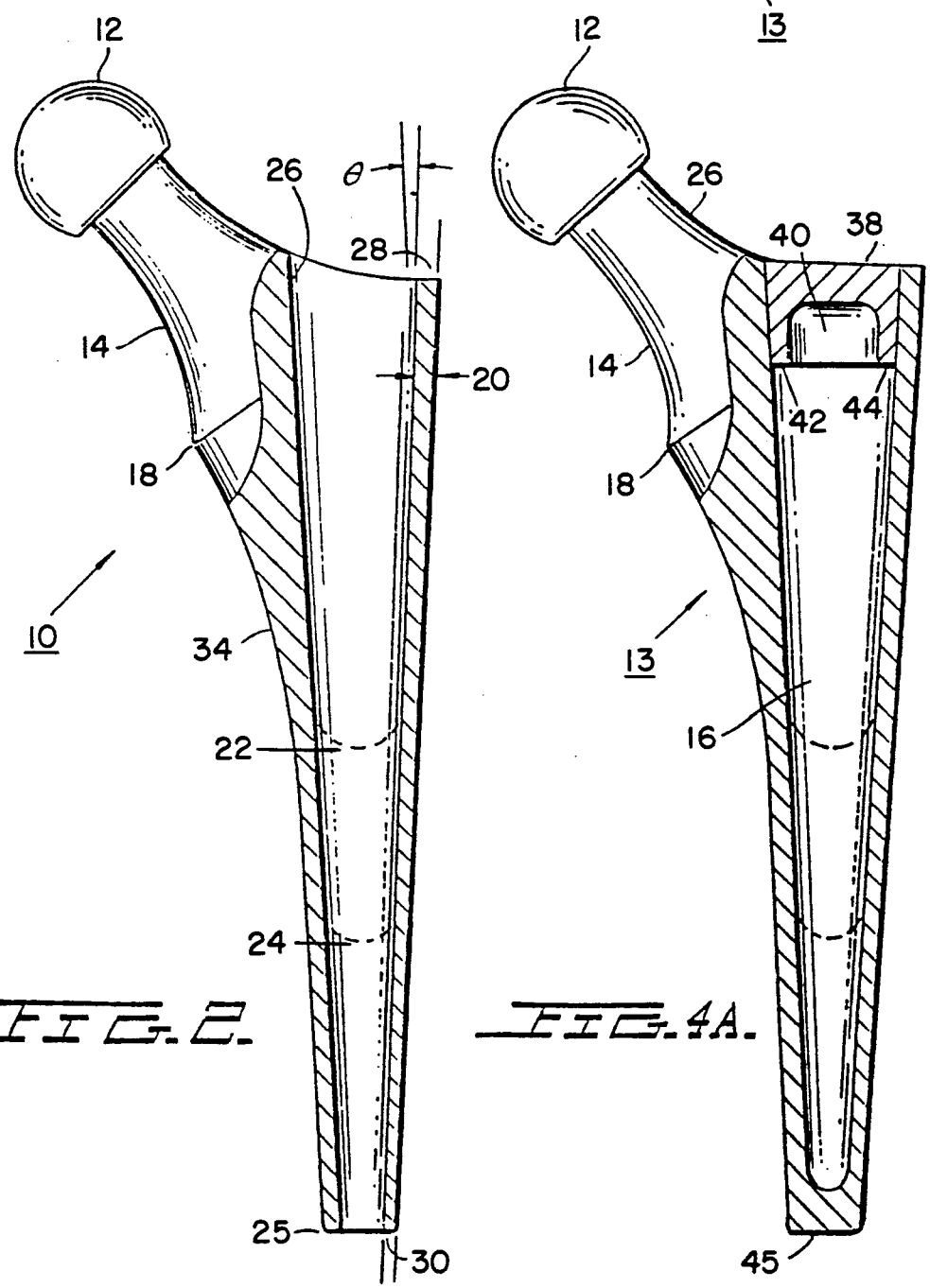

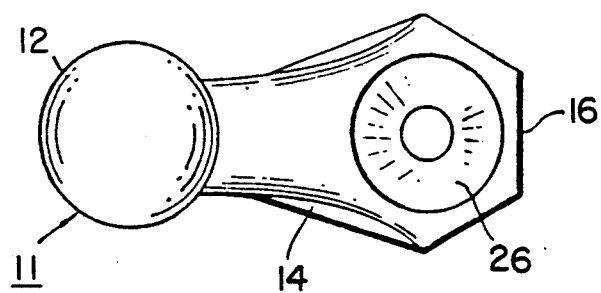
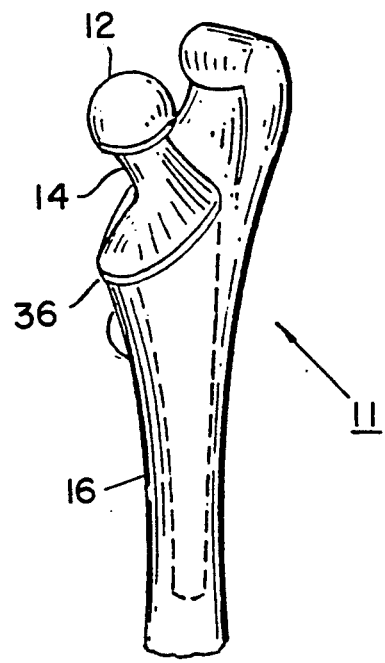
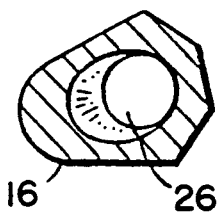
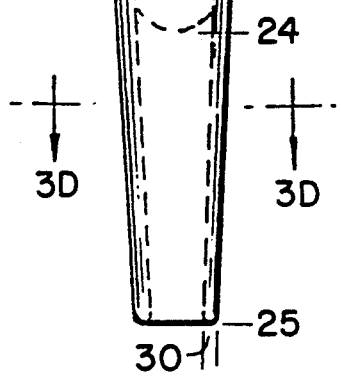
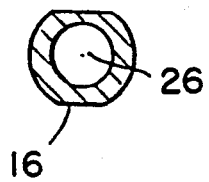

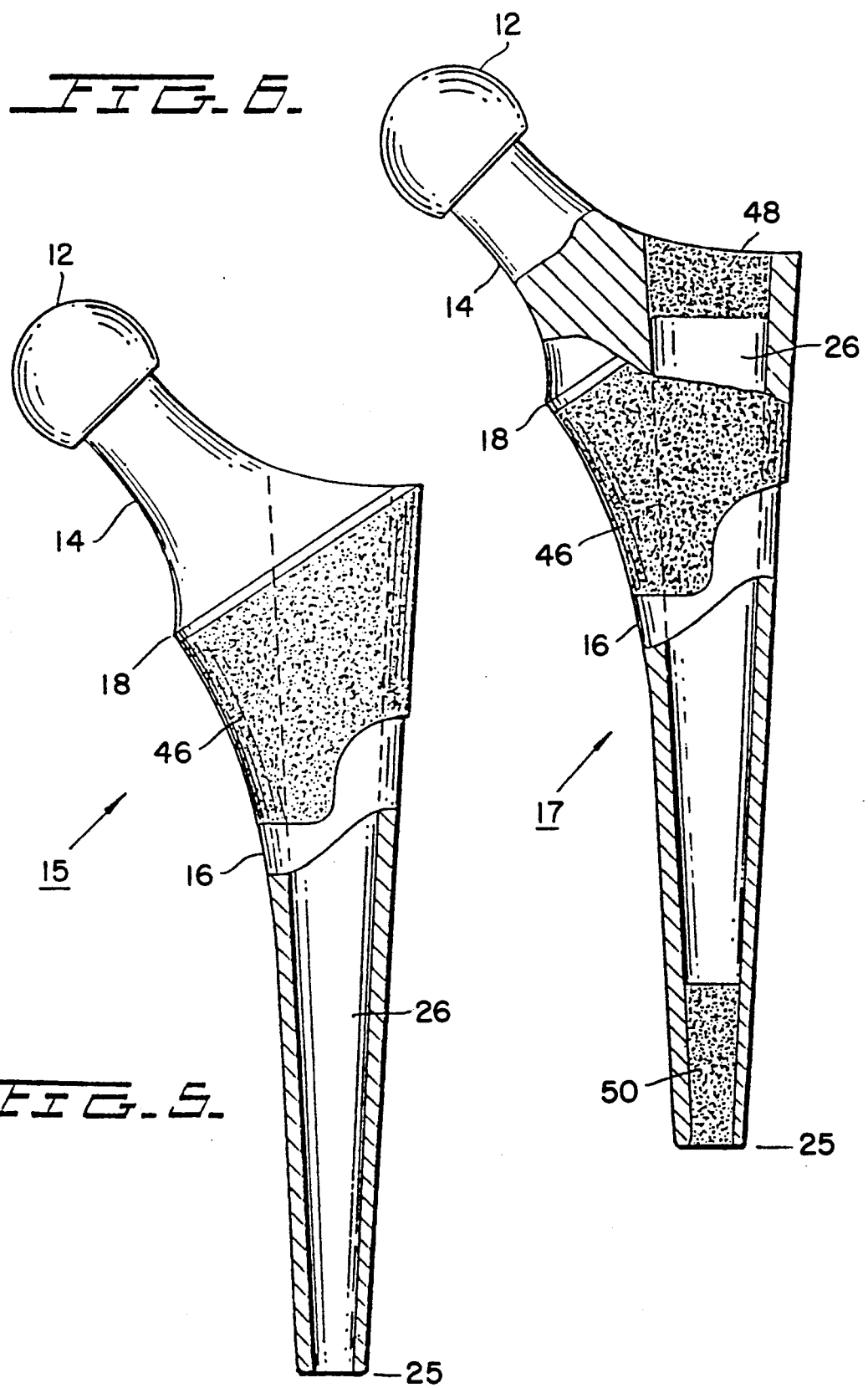

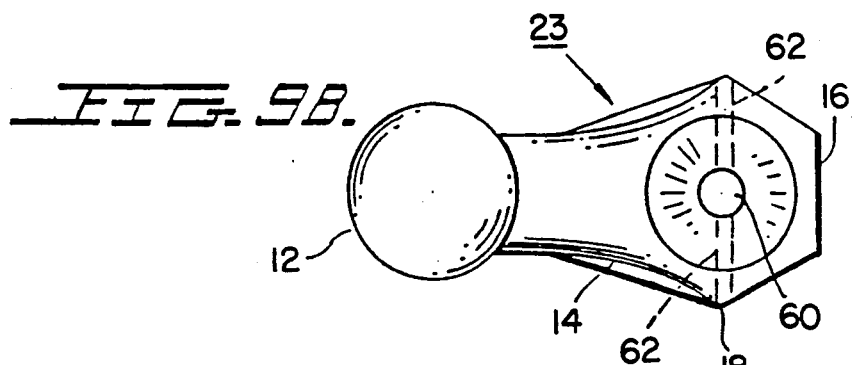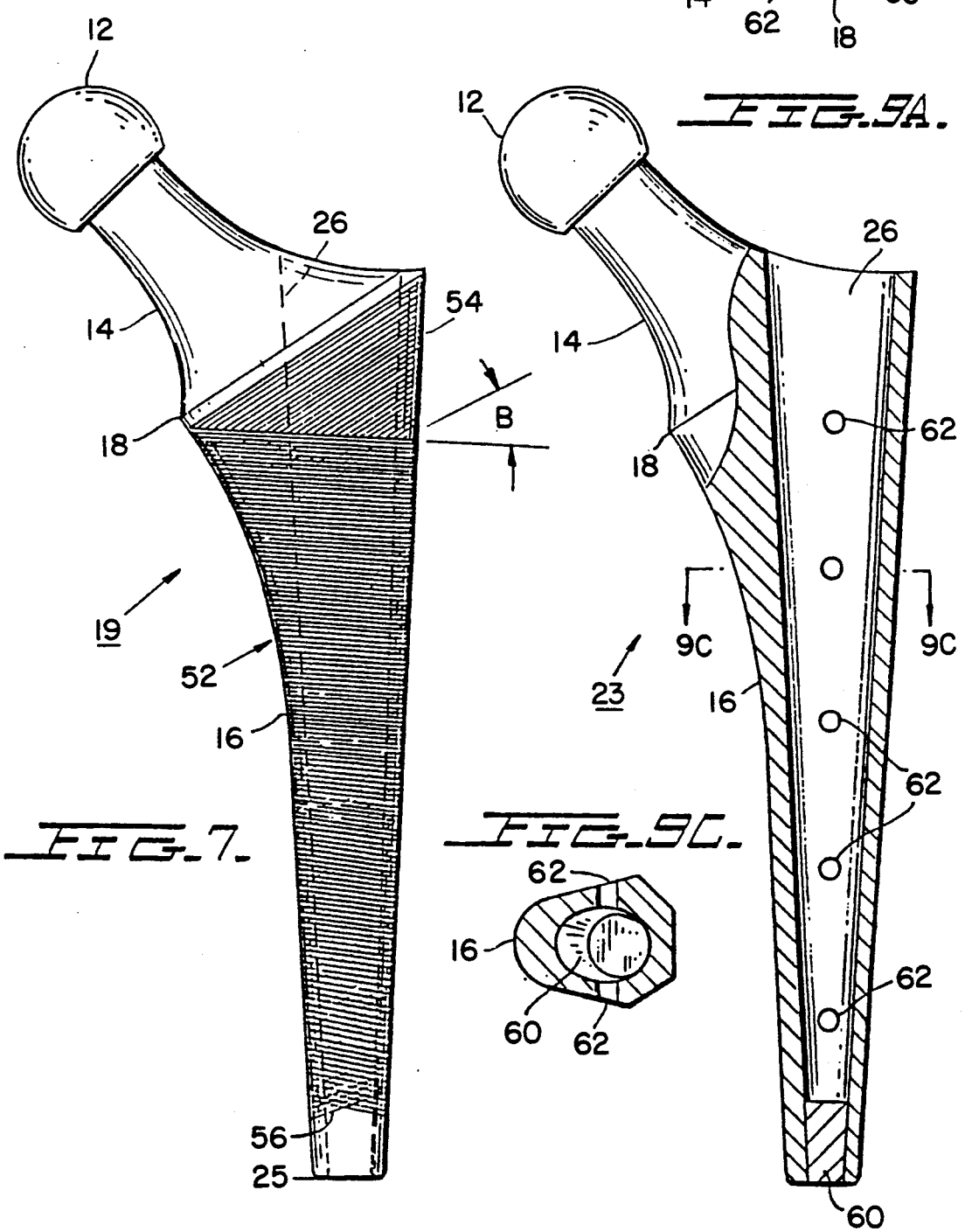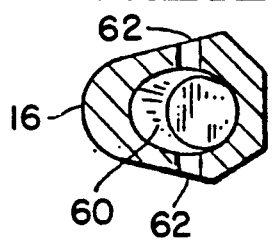

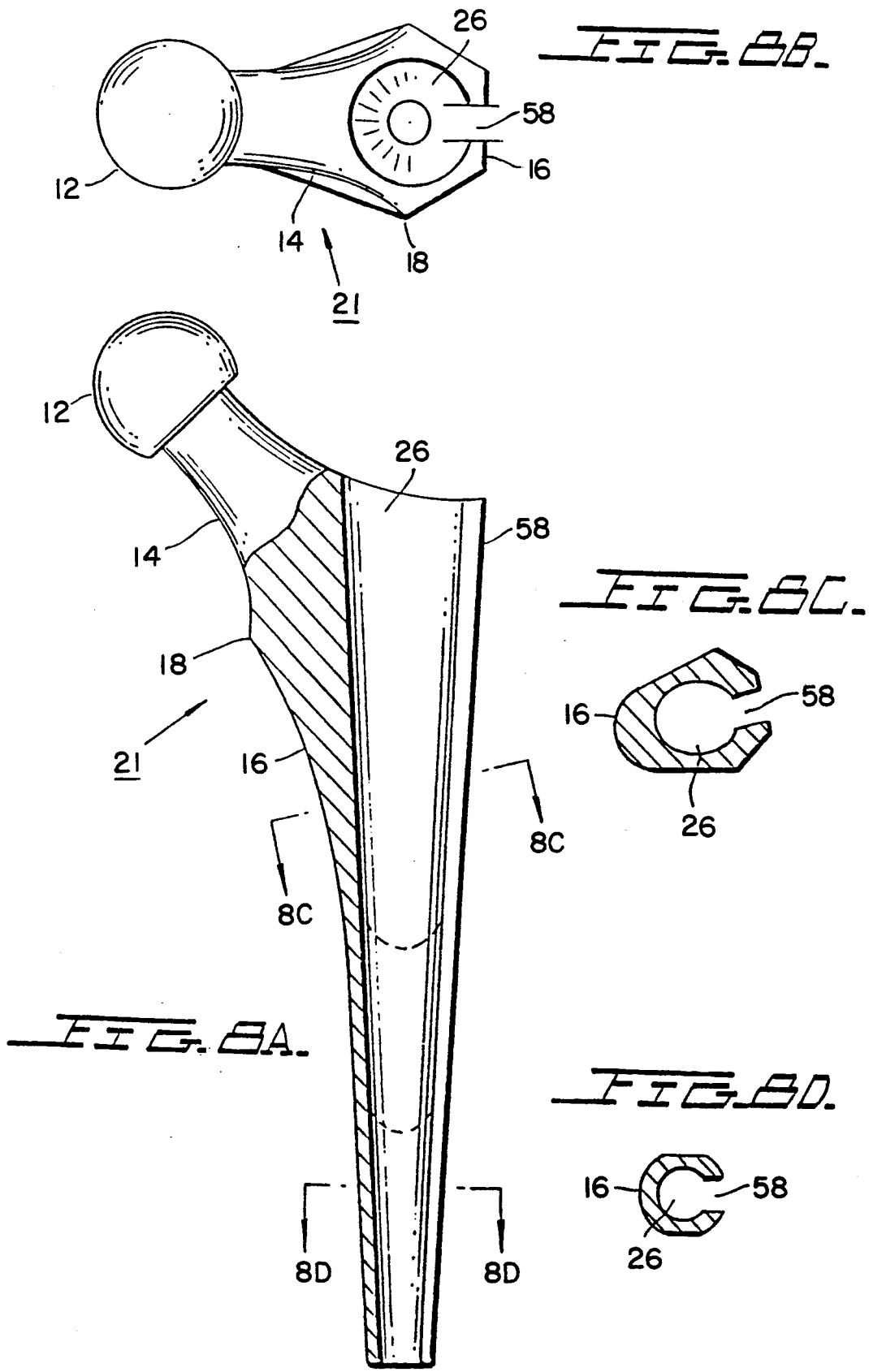

PROSTHESIS WITH FLEXIBLE INTRAMEDULLARY STEM

This application is a continuation of application Ser. No. 07/171,373, filed Mar. 21, 1988, now abandoned, which is a continuation-in-part of Ser. No. 06/849,172 filed Apr. 7, 1986, now abandoned.

BACKGROUND OF THE INVENTION

This invention relates, generally, to a prosthesis and more particularly to a bone prosthesis having an intramedullary fixation stem which is somewhat flexible and also comparable in flexibility to that of the surrounding supportive cortical bone. This structure gives great advantages and overcomes the difficulties encountered with prior art devices as will be more fully described and explained herein below.

Heretofore, prosthesis components and particularly femoral prosthesis components which are utilized for surgical reconstruction of a human hip joint have incorporated solid and relatively stiff intramedullary fixation stems. These stems are fabricated of suitable, compatible metallic alloys and are generally integral with the prosthetic neck and head portions. Therefore, the stems of these components are stiff, that is, they do not provide significant flexure along the length of the stem. However, the surrounding support of cortical bone within which they are implanted does offer some flexibility. Therefore, stiff stems, relative to the more flexible structure of the cortical bone, result in a composite structure wherein the flexural rigidity of the constituent parts varies significantly, depending upon prosthesis stem factors related to sectional size, shape, thickness and material modulus of elasticity.

The use of relatively stiff intramedullary stems has been clinically suspect of producing adverse and destructive bone reactions over a long period of time. More particularly, stiff stems can be attributed to producing micromotion at the stem and bone interface and can also be attributed to the development of reduced levels of force or stress shielding within the surrounding support of bone structure. Both the presence of interface micromotion and reduced bone stresses can result in adverse bone reactions which have been attributed to the diminution of bone mass at the interface and also within the surrounding bone matrix. Understandably, loss of bone is detrimental to the function of the implant and can produce loosening of the prosthesis and accompanying loss of articular joint or hip function and also results in severe pain. Depending upon the severity of these functional factors, surgical revision may be indicated.

The reaction forces between an implant stem and supportive bone are preferably distributed in such a manner that the greater forces are transferred proximally and decrease uniformly along the length of the fixation stem distally. This force distribution allows a greater proportion of joint reaction force to be transferred to the surrounding supportive cortical bone to levels comparable to that of an intact femur. It is most important for maximum advantages to have a uniformly flexible stem with relatively greater flexibility proximately than distally.

This therefore avoids adverse postoperative bone reaction which has been attributed to the stress shielding phenomenon of relatively stiff conventional hip stems. However, conventional relatively stiff stems reduce the forces distributed to surrounding bone to levels significantly below normal anatomical levels of an intact femur. Therefore, under the influence of reduced levels of bone stress distribution incident to stiff conventional stems, adverse bone reaction may occur postoperatively where the adjacent bone structure degenerates, diminishes or atrophies. This resultant bone loss can seriously affect the structural integrity of the adjacent supportive bone and may ultimately lead to significant loss or compromise of stem fixation. The loss of stem fixation will eventually compromise the long-term function of the implant prosthesis if the resulting pain and/or also loss of function becomes significantly intolerable to the patient.

The present invention therefore incorporates a flexible fixation stem which is integral to the metal prosthetic component neck and head portions. This stem flexibility significantly reduces the micromotion at the stem and bone interface while increasing the levels of force transferred to the adjacent supportive bone structure. This reduction of interface micromotion and the attainment of higher levels of bone force or stress over the entire bone can significantly improve the attainment and sustainment of stem fixation in a number of cementless modes, such as bony ingrowth fixation or press fit fixation. Heretofore the use of relatively stiff stems as are present in prior art and known devices now in use compromised good long-term results in hip joint reconstruction, where the adjacent bone has been adversely affected by the presence of intolerable micromotions at the fixation interface and from stress shielding within the adjacent supportive bone structure.

Accordingly, a number of devices have been utilized which attempt to provide a prosthesis having some flexibility. Examples of these devices may be found in U.S. Pat. Nos. 4,530,114, "Total Hip Joint Prosthesis", issued July 23, 1985 to Tepic; 4,287,617, "Femoral Pin for Hip Prosthesis", issued Sept. 8, 1981 to Tornier; 4,261,063, "Titanium or Titanium Alloy Pin to be Fixed in Long Bones", issued Apr. 14, 1981 to Blanquaert; 3,965,490, "Femural Insert for Hip Joint Prosthesis", issued June 29, 1976 to Murray et al: and 3,893,196, "Body Implant Material", issued July 8, 1975 to Hochman.

The Tepic reference provides for flexure through the use of tension transmitting wires. The Tornier reference utilizes bent sheet metal having a longitudinal slit therein, in an attempt to give the prosthesis some elasticity or flexibility. The Blanquaert reference utilizes a lattice of titanium wire in an attempt to have a modulus of elasticity close to that of the cortical bone tissue. The Hochman reference, while directed to an implant material, attempts to produce an implant material having a moduli of elasticity which is comparable to that of the cortical bone.

The Tornier reference shows a U-shaped sheet metal femoral compnent with an opening on the lateral side. The reason for this design is to provide a relatively stiff proximal end. The shape is designed with the objective to provide transverse elasticity, thus having the intent of facilitating positioning of the stem into the medullary canal and thus give a tight fit with the anticipated advantage of a certain "springiness" to the inserted device.

The Hochman et al patent describes a graphite or boron fiber-plastic composite fabrication of several conventional hip prosthesis design, a hip facture fixation device and an intramedullary fracture fixation rod for long bones. The stem portion of the prosthesis will be somewhat more flexible than its equivalent metal counterpart, but this is accomplished in a different manner by utilizing a more compliant, flexible material of construction.

Other prior art which attempts to disclose and describe devices similiar to, related to, or having one or more features of this invention include, U.S. Pat. Nos. 2,066,962, "Shaft for Golf Clubs or the Like", issued Jan. 5, 1937 to Cross; 4,375,810, "Joining Element for Fixation of Bone Tissues", issued Mar. 8, 1983 to Belykh et al; and 4,562,598 "Joint Prosthesis" issued Jan. 7, 1986 to Kranz; German patent no. 2,933,237 to Hoogeveen et al; French patent no. 2,483,218 to Cuilleron; German patent no. 2,636,644 to Heibler et al; German patent no. 2,558,446 to Pifferi et al; German patent no. 2,015,324 to Timmermans et al; European patent no. 0065481 to Anapliotis et al and European patent no. 0077868 to Godolin.

None of these devices describe or suggest the invention of this application or the devices described and claimed herein.

The Hoogeveen et al patent describes a hollow stem which has a modulus of elasticity conforming to the modulus of the surrounding bone. First of all, in this patent, the term "modulus of elasticity" is somewhat incorrectly used. It represents a property of an elastic material such as metal or bone which is the ratio of stress to strain. By using such a term, the inventor has inferred that the stem of invention device has a stiffness or flexibility of that of the surrounding bone. Thus, the inventors state that in their device the shank component in the proximal section must have particularly high rigidity from its contour and nature of the material. In the bottom section the shank should have only low rigidity, or only a low modulus of elasticity.

On the other hand and quite the opposite in structure, and result, in the device of this invention, the stem at the distal end may be intentionally solid and rigid. Preferably, for maximum cementless fixation advantage, the flexible end is the proximal end with more rigidity in the distal end to minimize interface shear and maximize low transfer to the supporting cortical bone as required to maintain stem support by osseous integration or press fit. If severe osteoporous is present, one advantage would be to have the entire stem flexible, since all the intact bone is flexible from bone (calcium) loss and flexual matching is especially important for the entire length of the device stem.

The Cuilleron patent shows a femoral prosthesis component which incorporates a sagittal slot. The stated purpose of this slot is to "make the stem elastic, expanding in the medullary canal so as to anchor it without the use of any sealing agent" (bone cement). The forces normally acting on the hip joint in use would in fact, react to close the split stem and therefore would obviously produce a loss of stem fixation from the ensueing collapse of the structure.

The Heibler et al patent describes a composite fiber hip prosthesis of carbon ceramic, $MOS_2$, or aromatic polyamide fibers combined with a compatible matrix of polyamides or expoxy resin. The hip stem has a hollow distal end to improve intramedullar fixation. Here again, the flexible portion is distally, not proximally used and is incorporated to improve stem fixation within the bone.

The Pifferi et al reference also does not suggest or describe the features of the invention and neither do the Timmermans et al Kranz, or Anapliotis patents relate to this invention except to generally disclose well-known hollow stem devices. The Godolin in European Patent shows a device in which the stem has incorporated therein an expansion screw-actuated taper mechanism to provide a tight fit within the medullary canal of the femur. Frusto-concial segments expand radially upon tightening of a screw-connected to an expansion cone and mandrel interface. Further, as described, the orientation of the frustro-conical segments are inappropriate to provide stability of the implant or preventing subsidence of and within the bone implantation in situ. If the screw arrangement were reversed, the operability of the device would be more positive.

However, all of these devices have one or more disadvantages in that they are expensive to manufacture, difficult to manufacture, unworkable from a clinical standpoint, or the like. Furthermore, none of them incorporate, describe, or suggest the devices disclosed herein for this invention nor do they give the advantages obtained by use of the herein described devices.

SUMMARY OF THE INVENTION

Therefore, it would be advantageous and it is an object of the present invention to produce a device which incorporates an integral, metallic alloy stem having a sectional design which provides flexural rigidity comparable to the surrounding support bone.

It is another object of the present invention to produce a composite structure of bone and metallic stem which are functionally identical in terms of bending and torsional deformation under the influence of active load forces.

It is still a further object of the present invention to produce a device having comparable flexural characteristics between the cortical bone and the metallic stem which will improve the long-term postoperative course of the prosthetic device.

It would also be advantageous to produce an implantable device which reduces, minimizes or eliminates the interface shear forces at the bone and stem interface.

It is also advantageous to produce an implant having a porous surface which is incorporated on the exterior surface of a flexible stem for ingrowth of bone to achieve fixation.

It is still a further object to produce a device which improves the quality of adjacent bone and/or the quality of the adjacent bony ingrowth while significantly reducing the postoperative time for subsequent bone remodeling to occur.

It would also be advantageous to produce a prosthesis which improves the distribution of the interface reaction forces between the stem and the bone.

It would also be advantageous to produce a hip or joint prosthesis, having a first portion for use exterior to a bone and a second portion contoured to be disposed within a bone, characterized in that the second portion is generally annular and axially tapering from a first diameter adjacent the first portion. The second portion has a bore in a portion thereof wherein the bore provides flexibility of the second portion which is comparable to the bone in which the second portion is disposed. Such a device is taught by the present invention.

BRIEF DESCRIPTION OF THE DRAWINGS

Reference is now made to the accompanying figures, in which:

FIG. 1A is an elevational view of the hip implant prosthesis of the present invention;

FIGS. 1B, 1C and 1D are top and cross-sectional views, respectively, of FIG. 1A;

FIG. 1E is a cross-sectional view of the implant of FIG. 1A when in a femur;

FIG. 2 is a cross-sectional view through the implant of FIG. 1A;

FIG. 3A is a side elevational view of an alternate embodiment of the present invention illustrating a collar portion;

FIGS. 3B, 3C and 3D are top and cross-sectional views, respectively, of FIG. 3A;

FIG. 3E is an illustrative view of the implant of FIG. 3A when disposed in a femur;

FIG. 4A is a cross-sectional view of an alternate embodiment of the implant of the present invention showing how the bore therein is sealed;

FIG. 4B is a top view taken through FIG. 4A;

FIG. 5A is another alternate embodiment of the present invention illustrating a porous surface;

FIG. 6A is an elevational, partly cross-sectional view of a further alternate embodiment of the present invention showing an external porous surface and proximal and distal internal porous surfaces;

FIG. 7A is an additional alternate embodiment of the present invention shown in elevation and having a filament wound thereon;

FIG. 8A is a cross-sectional view taken through another alternate embodiment of the present invention having a longitudinal slit therein;

FIGS. 8B, 8C and 8D are top and cross-sectional views, respectively, of FIG. 8A; and these figures are believed to incorporate many of the most important parts of the invention device.

FIG. 9A is still another alternate embodiment of the present invention showing openings in the stem; and FIGS. 9B and 9C are top and cross-sectional views taken through FIG. 9A, respectively.

DESCRIPTION OF THE PREFERRED EMBODIMENTS

Referring now to FIG. 1A, there is shown a side elevational view of a hip joint prosthesis of the present invention. The prosthesis or implant is shown generally at 10 and has at one end a femoral head 12. The neck portion 14, which may be considered as facing the medial side of the prosthesis 10, forms an intermediate portion between the femoral head 12 and a collarless transition joint at 18. The stem portion 16 has a bore 26 therein. The bore 26 may extend to different depths in the stem 16 as indicated by first bore depth 22, second or intermediate bore depth 24 or a bore through the distal end at 25.

The stem 16 is of a certain wall thickness 20 and generally tapers at a taper angle Theta ($\theta$). The taper angle Theta ($\theta$) may vary up to 5° which therefore results in an upper wall thickness 28, an intermediate wall thickness 29, and a distal wall thickness 30 which may be uniform or different from each other. It is this wall thickness 20, which may be considered as being disposed in a radial manner, and the bore 26 which aid in providing flexibility of the stem. It has been found that the ratio of internal diameter to outside diameter can be varied, depending upon the stiffness desired, and it preferably ranges up to 0.95 inches per inch, relative to the distal end as desired. Additionally, the stiffness along the stem 16 length may be varied by adjusting the depth of the internal cavity and hence partial depths 22, 24 and 25 may be employed. By referring to FIGS. 1B, 1C and 1D, the wall thickness 20 may be more clearly seen. Further, the distal end of the stem 16 is tapered at an angle alpha which preferably ranges up to 5 degrees.

Referring now to FIG. 1E, there is shown the implant of the present invention in use in a femur. Here, the stem 16 is disposed inside the femur 32 and forms a relatively snug fit which preferably forms a force fit therebetween. It is preferred that a press fit mode between the stem 16 and the bone 32 be utilized as opposed to the use of cement, although both modes are acceptable. The collarless transition joint 18 is disposed at the top part of the stem 16 just as the stem 16 emerges from the femur 32.

Accordingly, the prosthesis or implant 10 incorporates an integral metallic fixation stem of hollow construction. This is distinct from conventional, essentially more or less solid metallic fixation stems of the prior art. It has been found that by varying the sectional geometry, section thickness, material of construction and depth of the internal cavity or bore in the stem 16, predetermined levels of flexibility may be provided. It has also been found that by more closely approximating the flexibility of the adjacent support of cortical femoral bone, a significant reduction of interface micromotion between the bone 32 and the stem 16 will result. Also, a significant improvement in the level of stress developed between the surrounding bone structure will result. By reducing the interface micromotion as mentioned and improving bone loading so as to more closely match that of a natural femur, the prosthesis clinical performance and reliability may be improved. While the stem 16 may be manufactured of different materials, it is preferred that stainless steel, cobalt-chrome alloys or titanium alloys be utilized.

FIG. 2 shows a cross-sectional view taken through FIG. 1A. More clearly observable is the thickness 20 of the metal alloy 34.

Referring now to FIG. 3A, there is shown an alternate embodiment of the present invention. Here, the implant joint is shown generally at 11. This embodiment is essentially the same as that of FIG. 1, with the exception that a collared transition joint 36 is utilized. This collar 36 provides additional stem 16 support with respect to the medial bone shelf as shown in FIG. 3E. Also, as can be seen in FIGS. 3B, 3C and 3D, are the top and cross-sectional views of FIG. 3A which are essentially identical to that of FIG. 1.

Referring now to FIGS. 4A and 4B, an alternate embodiment of the present invention is shown at 13. Here, the implant 13 is generally the same as that of FIG. 1A with the exception that a proximal closure 38 is disposed at the top of the bore 26. The closure 38 is comprised of a closure bore 40 on the underside having closure extensions or legs 42, 44. Therefore, the closure 38 may be force-fit into the bore 26 and allows for the extensions 42, 44 to "collapse or compress" slightly. Disposed at the distal end of the stem 16 is an integral distal closure 45 which is formed when the bore 26 is not drilled to the extent shown in FIG. 1A. The bore 26 is closed in the manner shown so as to prevent the possible capture of biological fluids in certain clinical situations where the patient is at high risk of infection.

Referring now to FIG. 5, a porous implant is shown generally at 15. This implant is essentially the same as in FIG. 1A with the exception that a portion of the stem 16 has a porous surface 46. This porous surface 46 provides a conventional tissue ingrowth type of implant. Therefore, ingrowth of bone into the integral porous surfaces may be achieved since the present invention provides implant stability, as well as maintaining close proximately to adjacent bone, as previously mentioned. Therefore, use of the porous surface 46 in conjunction with the flexible stem 16 will substantially improve ingrowth mechanics due to the reduced mocromotion of the stem 16 and bone interface. This will also result in reduced postoperative time to achieve bone remodeling and ingrowth. Additionally, this combination may provide improved structure and strength of the ingrowing and surrounding bone.

Referring now to FIG. 6, a porous implant having open ends is shown generally at 17. This implant 17 is essentially the same as that in FIG. 5 with the exception that a proximal end porous surface 48 is disposed at the top of the bore 26 while a distal end porous surface 50 is at the lower end of the stem 16. The presence of the partial porous surfaces 48 and or 50, within the bore 26 is utilized to enhance stem fixation by enhancing resistance to transverse movement as well as subsidence or sinking instability. These interior and exterior porous surfaces consist of conventional types of interfused spherical compatible metallic particles and are preferably in the 200-800 micron range.

The concept of a macro surface structure or a micro surface structure such as a porous coated surface at the proximal end, where the section is relatively equal in flexibility as compared to the adjacent bone, is of great importance. The concept is also important with respect to the relative rigidity at the distal end of the device.

As a typical and most important, defined and descriptive detail, and improvement, the device is somewhat larger at the proximal end and tapered somewhat to a smaller portion at the distal end. This form provides great advantages for the invention.

Referring now to FIG. 7, a filament type prosthesis or implant is shown generally at 19. This implant 19 is structurally the same as FIG. 1 with the exception of filament 52 which is wound onto the stem 16. The filament 52 is wound in separate directions so as to be essentially in a biased first direction 54 and a biased second direction 56. The two biased elements 54, 56 are biased with respect to each other at an angle Beta ($\beta$) which preferably may be in a range of up to 45°. The filament 52 is a small diameter metallic or nonmetallic biologically compatible material, such as 6 AL-4 V titanium alloy or carbon, which are conventional materials available from a number of manufacturing sources. The spacing between adjacent windings of the filament 52 may be adjusted up to 1 mm so as to provide a lattice structure for tissue ingrowth fixation. Further, the filament winding 52 may provide or augment the structural strength of the stem 16, particularly in those situations where section thickness 20 is ½ millimeter or less. However, this does not totally define or comprise the invention and the device design.

Referring now to FIGS. 8A-8D a compressible implant is shown generally at 21. Here, the overall structure is similar to that of FIG. 1A. However, as can be seen from FIGS. 8B, 8C and 8D, a longitudianl slit or opening 58 is formed in one side of the outer wall. This lateral opening or slit 58 may extend through the entire stem 16 or may only go as far as bore depths 22 or 24 or 25 as shown in FIG. 1A. This slit 58 extends from the exterior of the stem 16 through the wall and to the bore 26. It should be pointed out that it is most important and in fact vital to achieve the advantages of this invention, to have the opening of the stem device on the lateral side for improved torsional constraint once bone infiltration has occurred. Furthermore, an opening on the medial side can detract from the bearing area between the stem and bone producing indesirable high unit loading proximally. This also is a very important difference and distinction over prior art devices. The opening 58 reduces the radial stiffness at a given transverse section, thereby enhancing the interference or wedge fit of the stem 16 with the cortical bone. The longitudinal opening 58 may also reduce the resultant hoop stresses within the cortical shaft during press fitting, thereby minimizing interoperative harm from premature bone fracture. Again, the implant 21 is made of stainless steel, cobalt-chrome alloys or titanium alloys which have been milled or cast accordingly. The longitudinal opening or slit 58 also enhances the torsional stability or fixation of the hip implant 21. Further, the channel or spacing allows bone remodeling through an intrusion of the bone therein. The depth and the length of the groove or slot may be continuous or interrupted or inclined. Additionally, the width of the opening 58 may vary and is preferably from 1-10 millimeters.

Referring now to FIGS. 9A-9C, a perforated implant is shown generally at 23. The overall shape of the implant 23 is similar to that of FIG. 1A. A distal end closure 60 is at one end of the bore 26. At various heights along the stem 16, there are provided openings 62 which are preferably on the anterior and posterior aspects of the stem 16. The bore 26 and openings 62 are provided for storage and in-vivo release of various bioactive substances to enhance bone remodeling postoperatively. The openings 62 also provide the chance for the storage and subsequent release of antibiotic substances in instance where the patient is at high risk of infection. These openings 62 extend through to the bore 26 in the stem 16, as shown in FIGS. 9B and 9C.

It is to be understood that many variations of the present invention may be practiced without departing from the spirit and scope of the present invention. For example, different types of femoral heads may be utilized while the implant may be utilized in different portions of the body, such as the shoulder or knee joint. Further, slightly different shapes or proportions may be utilized while different materials for the implant may also be used.

Although the present invention has been described in connection with a plurality of preferred embodiments thereof, many other variations and modifications will now become apparent to those skilled in the art. It is preferred, therefore, that the present invention be limited not by the specific disclosure herein, but only by the appended claims.

What is claimed is:

1. A hip prosthesis comprising:
   a stem for implantation into a femur, said stem having a proximal end and a distal end, said stem having a longitudinally extending tapered bore therein which is open along a centerline thereof and which is defined by a surrounding wall and extending from said proximal end at least part way to said distal end, said stem having a lateral side and a medial side, said wall at said lateral side and at said proximal end having a thickness less than that at said medial side and at said proximal end, said stem having a flexibility close to the flexibility of at least the distal end of the femur within which it seats and said stem being substantially free of mechanically induced, pre-loaded compressive stresses other than those produced by normal human anatomy when operatively assembled in the femur; and a femoral head for implantation into a hip socket and connected with said stem at the medial side thereof.

2. A hip prosthesis according to claim 1, wherein said wall of said stem has a thickness which tapers in a direction extending from said proximal end toward said distal end.

3. A hip prosthesis according to claim 2, wherein said wall tapers at an angle up to 5°.

4. A hip prosthesis according to claim 1, further comprising a neck portion connected between said femoral head and said stem.

5. A hip prosthesis according to claim 4, further including collared transition joint means connected between said neck and said stem for providing additional support of said prosthesis with respect to said femur.

6. A hip prosthesis according to claim 1, further including filament means circumferentially disposed on at least a portion of said stem for augmenting the strength of said stem and for facilitating ingrowth of the bone material of said femur onto said stem.

7. A hip prosthesis according to claim 1, wherein said stem further includes at least one aperture in the wall of said stem and in communication with said bore to permit dispersal of bioactive substances in said stem.

8. A hip prosthesis according to claim 7, wherein said bioactive substances are disposed in said at least one aperture in said stem.

9. A hip prosthesis according to claim 1, further including a porous coating on an exterior surface of said stem.

* * * * *